United States Patent
Joensuu et al.

(10) Patent No.: US 12,044,607 B2
(45) Date of Patent: Jul. 23, 2024

(54) MONITORING AND CONTROLLING HYDROPHOBIC COMPONENTS IN A PULP PROCESS

(71) Applicant: KEMIRA OYJ, Helsinki (FI)

(72) Inventors: Iiris Joensuu, Espoo (FI); Marjatta Piironen, Espoo (FI); Andy Bergeron, Atlanta, GA (US); Travis Bjerketvedt, Atlanta, GA (US)

(73) Assignee: KEMIRA OYJ, Helsinki (FI)

( * ) Notice: Subject to any disclaimer, the term of this patent is extended or adjusted under 35 U.S.C. 154(b) by 455 days.

(21) Appl. No.: 17/418,510

(22) PCT Filed: Dec. 20, 2019

(86) PCT No.: PCT/FI2019/050921
§ 371 (c)(1),
(2) Date: Jun. 25, 2021

(87) PCT Pub. No.: WO2020/136308
PCT Pub. Date: Jul. 2, 2020

(65) Prior Publication Data
US 2022/0146396 A1    May 12, 2022

Related U.S. Application Data

(60) Provisional application No. 62/785,862, filed on Dec. 28, 2018.

(30) Foreign Application Priority Data

May 27, 2019   (FI) ...................................... 20195437

(51) Int. Cl.
*G01N 15/06*   (2024.01)
*G01N 15/075*  (2024.01)
*G01N 33/34*   (2006.01)

(52) U.S. Cl.
CPC ........... *G01N 15/06* (2013.01); *G01N 33/343* (2013.01); *G01N 15/075* (2024.01)

(58) Field of Classification Search
CPC ............... G01N 15/06; G01N 15/0255; G01N 2015/0053; G01N 2015/0693; G01N 21/64; G01N 21/85; G01N 33/343
See application file for complete search history.

(56) References Cited

U.S. PATENT DOCUMENTS 5,940,177 A * 8/1999 Esser .................. G01N 33/343
                                                      356/73
6,214,560 B1 * 4/2001 Yguerabide ......... G01N 33/585
                                                      506/3
(Continued)

FOREIGN PATENT DOCUMENTS

CN            1223692 A *   7/1999   ........... C12Q 1/6816
CN          101622536 A     1/2010
(Continued)

OTHER PUBLICATIONS

Finnish Search Report issued in corresponding Patent Application No. 20195437dated Sep. 9, 2019.
(Continued)

*Primary Examiner* — Michael A Lyons
(74) *Attorney, Agent, or Firm* — Espatent Oy

(57) ABSTRACT

A sample of an aqueous stream is conducted to an optical measurement device. A hydrophobic dye is added. The sample is fractionated into fractions according to particle size or mass. Fluorescence intensity values and light scattering intensity values for the fractions are measured. Fluorescence intensity values of the fractions are added together thus obtaining a sum of the fluorescence intensity values. Light scattering intensity values of the fractions are added together, thus obtaining a sum of the light scattering intensity values. A hydro-phobicity density of the particles in the (Continued)

sample, is calculated by dividing the sum of the fluorescence intensity values with the sum of the light scattering intensity values. A concentration of hydrophobic contaminants in the aqueous stream is monitored and controlled based on the calculated hydrophobicity density of the particles in the sample.

19 Claims, 6 Drawing Sheets

(56) References Cited

U.S. PATENT DOCUMENTS

| | | | |
|---|---|---|---|
| 9,562,861 | B2 | 2/2017 | Von Drasek et al. |
| 2008/0151227 | A1 | 6/2008 | Champ et al. |
| 2009/0260767 | A1* | 10/2009 | Gerli .................... G01N 33/343 |
| | | | 162/49 |
| 2010/0012284 | A1* | 1/2010 | Kaub .................... G01N 33/343 |
| | | | 162/49 |
| 2012/0258547 | A1 | 10/2012 | Von Drasek et al. |
| 2015/0114094 | A1* | 4/2015 | Vahasalo ................ G01N 15/06 |
| | | | 73/61.71 |
| 2015/0147814 | A1 | 5/2015 | Joensuu et al. |
| 2021/0156092 | A1* | 5/2021 | Piironen .................. D21C 9/08 |

FOREIGN PATENT DOCUMENTS

| | | | | |
|---|---|---|---|---|
| CN | 101910515 | A | | 12/2010 |
| CN | 102356313 | A | | 2/2012 |
| CN | 103608515 | A | * | 2/2014 .............. D21C 9/00 |
| CN | 103743610 | A | * | 4/2014 |
| CN | 107636227 | A | | 1/2018 |
| EP | 3287763 | A1 | * | 2/2018 .............. D21C 9/08 |
| WO | 2007082376 | A1 | | 7/2007 |
| WO | 2013175077 | A1 | | 11/2013 |
| WO | 2015028711 | A1 | | 3/2015 |
| WO | 2015075319 | A1 | | 5/2015 |

OTHER PUBLICATIONS

International Preliminary Report on Patentability (PCT/IPEA/409) issued in corresponding International Application No. PCT/FI2019/050921 dated Apr. 13, 2021.

International Search Report (PCT/ISA/210) and Written Opinion (PCT/ISA/237) mailed on Mar. 20, 2020, by the Finnish Patent Office as the International Searching Authority for International Application No. PCT/FI2019/050921.

Yongli et al. EN machine translation and original Chinese: Study on the characteristics of organic matter in biochemical effluent of papermaking wastewater and its removal behavior in advanced treatment, pp. 89-93, Science and Technology, vol. 34, No. 5, 2015, DOI:10.19696/j.issn1671-4571.2015.05.020.

Genest et al. Removal of micro-stickies from model wastewaters of the paper industry by amphiphilic starch derivatives, Colloids and Surfaces A: Physicochemical and Engineering Aspects, 484 (2015), pp. 231-241.

* cited by examiner

MONITORING AND CONTROLLING HYDROPHOBIC COMPONENTS IN A PULP PROCESS

FIELD OF THE INVENTION

The present invention relates to a method and an apparatus for monitoring and controlling hydrophobic contaminants in an aqueous stream of a pulp or papermaking process.

BACKGROUND ART

Measurements of solid matter containing liquids are typical in forest industry, in which wood pulp samples or filtrates, such as wire water, white water, thickener filtrate or other pulp filtrate, or circulated water, are monitored in order to be able to control the overall process. The liquids used often contain solid matter that needs to be measured and monitored.

The measurement may be carried out off-line or on-line, where off-line methods often involve batch sampling and laboratory analyses. They enable providing accurate and versatile information on the suspension, but suffer from considerable time delays. On-line methods, on the other hand, provide instant or almost instant information on the suspension, but the data obtained is usually not as accurate as that achieved in the laboratory.

Liquids and filtrates in pulp industry contain particles the amount, type, and size distribution of which have a considerable effect on upcoming process stages. For example, pitch may cause running problems on paper machines.

One technique for analyzing papermaking process samples is a method where harmful particles, such as pitch, white pitch and stickies, that disturb the papermaking process causing production down-time and paper defects, are detected. The system fractionates the particles according to their mass and/or size. The fractionated samples are analyzed with optical measurements. The system measures the particle and/or mass distribution of a filtrate to detect paper machine problems.

SUMMARY

The following presents a simplified summary of features disclosed herein to provide a basic understanding of some exemplary aspects of the invention. This summary is not an extensive overview of the invention. It is not intended to identify key/critical elements of the invention or to delineate the scope of the invention. Its sole purpose is to present some concepts disclosed herein in a simplified form as a prelude to a more detailed description.

According to an aspect, there is provided the subject matter of the independent claims. Embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following the invention will be described in greater detail by means of preferred embodiments with reference to the attached drawings in which.

DETAILED DESCRIPTION OF EMBODIMENTS

Figure 1A:
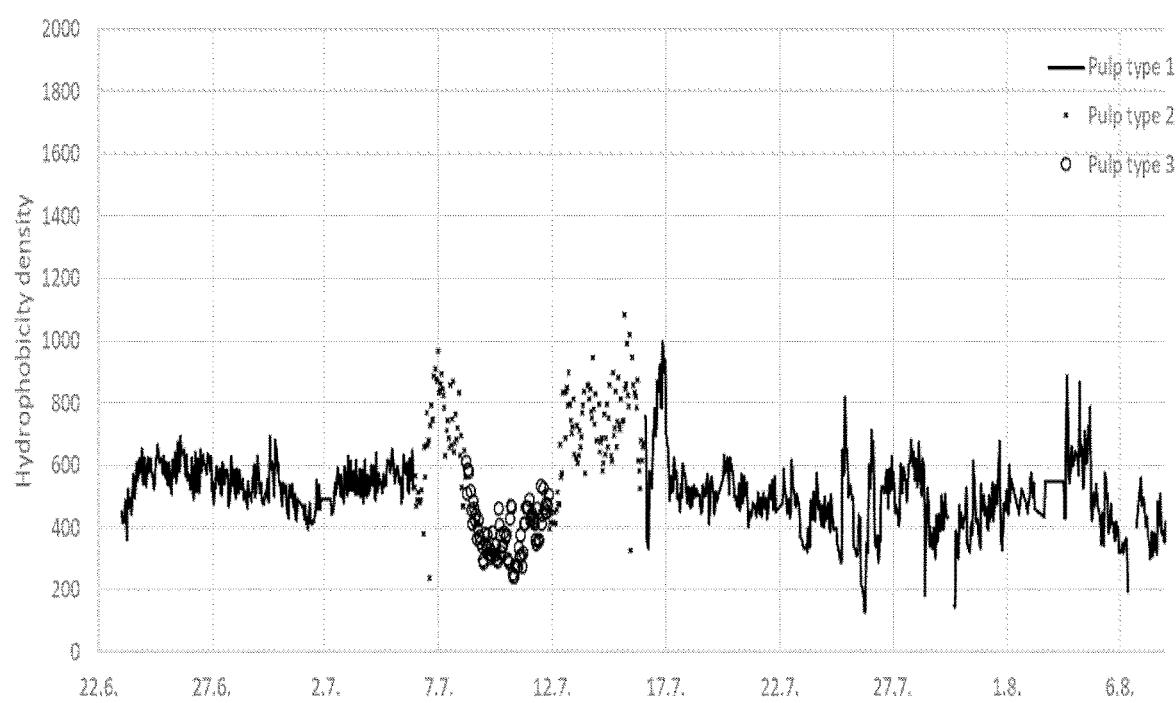
FIGS. 1A and 1B show the hydrophobicity density for different pulp streams measured over a time period.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising", "containing" and "including" should be understood as not limiting the described embodiments to consist of only those features that have been mentioned and such embodiments may contain also features/structures that have not been specifically mentioned.

If there are contaminants (extracts from pitch) in the pulp/mass after pulp production, these contaminants may appear as precipitates or deposits during papermaking.

Hydrophobic contaminants, such as wood pitch, are typically as single pitch particles and/or on the surface of other particles like fines and fibers in pulp samples (filtrates or suspensions). If only total hydrophobicity of a sample is measured or considered, and if hydrophobicity increases, then it is not known whether only the consistency of the sample increases (i.e. the amount of solid matter increases), and/or does the hydrophobicity increase, because the number of hydrophobic contaminants on the surfaces of particles increases (i.e. the concentration of wood pitch increases (mg/kg)) and/or the concentration of single pitch particles increases.

In order to monitor the concentration or density of hydrophobic contaminants (like wood pitch) in the pulp and/or filtrate, the relationship between hydrophobicity and particle count is calculated. This enables compensating the variations in pulp consistency (the total particle count directly correlates with the pulp consistency), and thus concentration of pitch and/or hydrophobicity density is found out. Hydrophobicity may be due either to increased pulp consistency (increased particle count) or due to increased pitch concentration. By compensating the changes in the pulp consistency by means of the hydrophobicity, changes in the pitch concentration may be monitored. The concentration of pitch has a direct effect on the quality of the end product: the higher the pitch concentration, the poorer the quality of the pulp, which may cause problems in further processing of the pulp.

So far, the concentration or density of pitch has been difficult to estimate. Hydrophobicity density (i.e. hydrophobicity index) describes the concentration of hydrophobic contaminants and/or the density of hydrophobic contaminants. The concentration or density of wood pitch may be defined as the mass of wood pitch divided by the volume or mass of a sample, for example, a milligram of wood pitch in a kilogram of solid matter (mg/kg), a milligram of wood pitch in a kilogram of dry solid of the sample (mg/kg), a milligram of wood pitch in a certain volume (like mg/l). The concentration may also be defined as the count of wood pitch divided by the volume of the sample, mass of solid matter in the sample or mass of dry solid in the sample.

Hydrophobic contaminants may be wood pitch.

An embodiment discloses a simple method and device for estimating the concentration of pitch and/or density of pitch in a pulp sample. If it is known that there are impurities in the pulp (or the pulp liquid), they may be affected by increasing the amount of washing water or by adding a chemical that disperses (stabilizes) pitch into small particles which may be removed from the mass by washing to avoid them being passed to the paper mill.

To monitor pitch concentration of a pulp suspension on a pulp machine, a monitoring unit may be installed on the white water tank or headbox. Pitch concentration monitoring may be performed on-line to predict or determine the need for adding control chemicals. The monitoring may be performed by using an online tool that monitors the relative particle size, relative count and relative hydrophobicity in the sample. Colloidal pitch particles in the wet end of the pulp drying machine may be monitored by on-line measurement that is able to separate the particles based on their size/mass and return a relative hydrophobicity value. The samples for continuous on-line monitoring may be taken from the white water chest or wire water of the pulp drying machine, since this is typically where the cycling up of the hydrophobic particles is the most prevalent.

A method and system for monitoring and controlling hydrophobic components in a pulp mill is disclosed. Thus a method and system for monitoring and controlling pulp purity/pulp impurities is provided.

An embodiment is related to the use of an online or portable measurement device or system in a pulp mill. The system measures the density/concentration of hydrophobic contaminants, i.e. hydrophobicity index, in the pulp sample and controls the chemical treatment of pulp streams and/or washing of the pulp, on the basis of the measured hydrophobicity index. The system may also be used for monitoring incoming pulp streams in a paper machine and for controlling a computerized deposit control program on the basis of the hydrophobicity index to control the concentration of hydrophobic contaminants in the pulp stream (or in dried pulp).

In an embodiment, specific measurement variable(s) are used for monitoring and/or controlling hydrophobic contaminants in pulp streams. The hydrophobicity density (i.e. the density of hydrophobic contaminants, i.e. a hydrophobicity index) is a consistency compensated hydrophobicity value. The hydrophobicity density enables more accurately to describe or characterize changes in the concentration of hydrophobic particles than the hydrophobicity value itself. The hydrophobicity value for a pulp stream or sample is a sum parameter of the count and density of hydrophobic contaminants. The effect of chemical treatment and washing of the pulp on pulp quality may more easily be discovered by monitoring the hydrophobicity density, due to the elimination of consistency variations in the measurement results of the measurement system. The total particle count correlates with the consistency of the pulp, i.e. the total particle count equals to the sum of the light scattering intensity values for all fractions of the pulp sample.

An exemplary method comprises continuously in repeating cycles conducting a sample to an optical measurement device, adding a hydrophobic dye to the sample, fractionating the sample into fractions according to particle size and/or mass, and measuring fluorescence intensity values and light scattering intensity values from the fractions. The method further comprises calculating a cumulative sum of the fluorescence intensity values and light scattering intensity values over the fractions, calculating the hydrophobicity density of the particles by dividing the cumulative sum of the fluorescence intensity values with the cumulative sum of the light scattering intensity values, using the hydrophobicity density of the particles for monitoring hydrophobic components in the pulp stream, and controlling the hydrophobic contaminants in the pulp by manual adjustment and/or automatic dosing of chemicals, and/or by pulp washing control.

Instead of a continuous process, the method steps may be performed at selected intervals or when desired. In that case the method comprises calculating the sum of the fluorescence intensity values over the fractions, calculating the sum light scattering intensity values over the fractions, calculating the hydrophobicity density of the particles by dividing the sum of the fluorescence intensity values with the sum of the light scattering intensity values.

Particles in the fractions may be, for example, colloids, fines, and fibers. The chemicals to be used may include dispersing agent(s), fixative(s), retention aid(s), surfactant(s) and/or detackifier(s), for example. The pulp washing may be controlled e.g. by controlling the use of washing water, or by controlling the use of washing chemicals such as dispersing agent(s).

The method may comprise calculating a cumulative sum of the fluorescence intensity signal for each of the fractions, calculating a cumulative sum of the light scattering intensity signal for each of the fractions, calculating the hydrophobicity density for each of the fractions (e.g. colloids fraction, fines fraction, agglomerates fraction, fibers fraction), using the specific information thus obtained for chemical treatment of pulp stream(s), e.g. for the selection of right chemical(s), for the selection of right dosage(s), and/or for automatic dosing control of chemical(s). The hydrophobicity density of the particles may be calculated by dividing the cumulative sum of the fluorescence intensity signal by the cumulative sum of the light scattering intensity signal. The hydrophobicity density of the particles may be used for monitoring and controlling the hydrophobic components in the pulp. Controlling of the hydrophobic contaminants may be manual adjustment and/or automatic dosing of chemicals such as dispersing agent(s), fixative(s), retention aid(s), surfactant(s) and/or detackifier(s) in the pulp, and/or controlling pulp washing, e.g. controlling the use of water or washing chemicals such as dispersing agent(s).

For example, the controlling of the use of water may include controlling the amount of wash water or how much fresh water is taken in and how much water is drained out (describes how much water circulation has been closed).

An exemplary method may comprise calculating a cumulative sum of the fluorescence intensity signal for each fraction, calculating a cumulative sum of the light scattering intensity signal for each fraction, calculating hydrophobicity density for each fraction (e.g. colloids, fines, agglomerates, fibers), using this specific information for chemical treatment of pulp stream(s) (e.g. by selection of right chemical(s), by selection of right dosage(s), and/or by automatic dosing control of chemical(s)).

In an embodiment, the pulp stream (or sample) is a dilute obtained by diluting dried pulp or high consistency pulp (for example, more than 1.5%) with water.

Thus, in an embodiment, a sample is taken from a selected filtrate water (or a very dilute pulp, low consistency pulp, for example, less than 1.5%) at the pulp mill, a dye is added, the sample is fractionated, and the hydrophobicity of all the fractions is measured. The light scattering and fluorescence intensities are measured from all the fractions, the fluorescence intensity values of all the fractions (which are present in the sample; typically there are no fibers present in the filtrate water) are summed up, the light scattering intensity values of all the fractions are summed up (the area), and the total sum of fluorescence intensity values is divided with the total sum of light scattering intensity values to obtain the hydrophobicity density which may also be referred to as the hydrophobicity index. The process may be a continuous process wherein a cumulative sum of the values over a selected period is obtained.

The hydrophobicity density, also referred to as the hydrophobicity index, thus obtained correlates well with the concentration of pitch in the sample. In the example situation shown in FIGS. 1A and 1B, the hydrophobicity index (hydrophobicity density) is at its highest when pulp type 2 is used. The same correlation would not be considered if only total hydrophobicity were considered.

It is also possible to calculate the hydrophobicity index for one fraction only. In that case the sum of fluorescence intensity values for said fraction is divided with the sum of light scattering intensity values for said fraction to obtain the hydrophobicity density for said fraction.

It is also possible to calculate the hydrophobicity index only for some of the fractions. In that case the sum of fluorescence intensity values for the selected fractions is divided with the sum of light scattering intensity values for said fractions to obtain the hydrophobicity density for said fractions.

In an embodiment, samples may be taken from an aqueous pulp stream at any part of the pulp or paper making process. For example, the samples may be taken from pulp suspensions, diluted pulp, pulp filtrates, filtrate water, dilute mass, white water, or wire water. In an embodiment, control chemicals or pulp washing water may be added to the aqueous stream at a desired part of the pulp or paper making process. For example, control chemicals may be added to the pulp stream (e.g. pulp washers, mixing chest, machine chest).

Thus pulp samples may be taken at different positions of the pulp production or papermaking process. For example, pulp may be manufactured and dried before transporting it to another manufactory, wherein during drying of the pulp, the low consistency pulp is on the wire (or between the wires) and water is removed from between the wire reels. If at that stage a sample is taken and analysed in the wire water, and if it is discovered that there is pitch in the wire water, chemicals may be added to pulp suspension(s) before the wire section to affect (i.e. to decrease) the amount (the concentration) of pitch.

An exemplary device continuously (or batchwise) measures the hydrophobicity index of the particles in a pulp stream, specifically in the white water stream in the pulp dryer.

By means of an exemplary embodiment, it is possible to monitor the change in the hydrophobicity index when the pulp is derived from different species of tree. It is also possible to reduce the hydrophobicity index in the pulp by increasing chemical (e.g. dispersant) dosage if required. For example, at bleaching stage it is possible to reduce the hydrophobicity index of pulp by increasing the amount of washing water. It is also possible to determine at which hydrophobicity index level the change in the chemical dosing and/or the change in the amount of dilution water is to be made.

By means of an exemplary embodiment, it is possible to detect changes in the hydrophobicity index. Cost savings may be achieved as it is possible to more accurately determine the right amount, point of time and/or process stage at which the chemical addition or water dilution/washing is to be carried out. Thus it is possible to avoid overdosing the chemicals. Product quality (i.e. pulp and/or paper quality) is improved, as less hydrophobic material (e.g. wood pitch) ends up in the end product. Real time data may be obtained on the process conditions, and a web based application may be provided.

Figure 4:
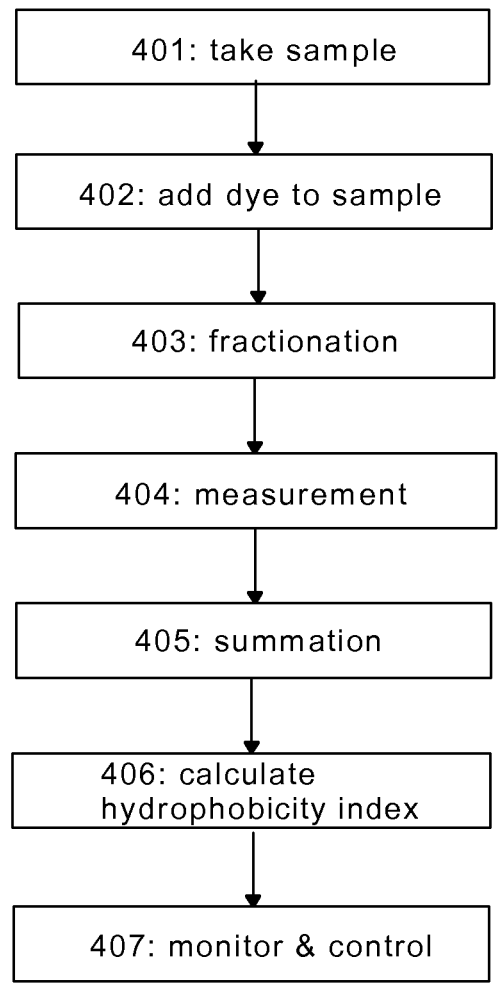
FIG. 4 illustrates an exemplary method.

FIG. 4 illustrates an exemplary method. Referring to FIG. 4, in item 401, an apparatus which may be an online device and/or a portable device takes a sample of an aqueous pulp flow. Alternatively, the sample may be taken from dried pulp or high consistency pulp, wherein the pulp sample is then diluted with water. In item 402, the apparatus adds hydrophobic dye to the sample, and in item 403 the apparatus performs fractionation into fractions of the sample based on size and/or mass. The fractionation may be performed e.g. by means of field flow fractionation. It is also possible that the dye addition is performed only after the fractionation by adding the dye to the individual fractions. In item 404, the apparatus performs optical measurement on the fractions thereby obtaining fluorescence intensity and light scattering intensity values for each of the fractions. The fluorescence intensity and light scattering intensity are measured as a function of time, thereby obtaining multiple values of fluorescence and light scattering for each fraction. Measuring frequency of fluorescence intensities and light scattering intensities may be, for example, once per second. In item 405, the method comprises performing in the apparatus the steps of adding together the fluorescence intensity values of the fractions thus obtaining a sum of the fluorescence intensity values, and adding together the light scattering intensity values of the fractions thus obtaining a cumulative sum of the light scattering intensity values. In item 406 the hydrophobic index is calculated in the apparatus by 1) calculating a hydrophobicity density of the particles in the sample by dividing the sum of the fluorescence intensity values with the sum of the light scattering intensity values, and monitoring and controlling the amount of hydrophobic contaminants in the aqueous stream based on the calculated hydrophobicity density of the particles in the sample, and/or 2) calculating a hydrophobicity density of the particles in the fraction by dividing the sum of fluorescence intensity values of the fraction with the sum of light scattering intensity values of the fraction, and monitoring and controlling the amount of hydrophobic contaminants in the aqueous stream based on the calculated hydrophobicity density of the particles in the fraction. For example, the apparatus may be configured to send a control signal to dosing means to dose chemical(s) and/or washing water to the pulp if so required based on the hydrophobicity density. If the apparatus repeats the process e.g. at predetermined time intervals, calculations for the hydrophobicity index may be performed cumulatively.

Figure 5:
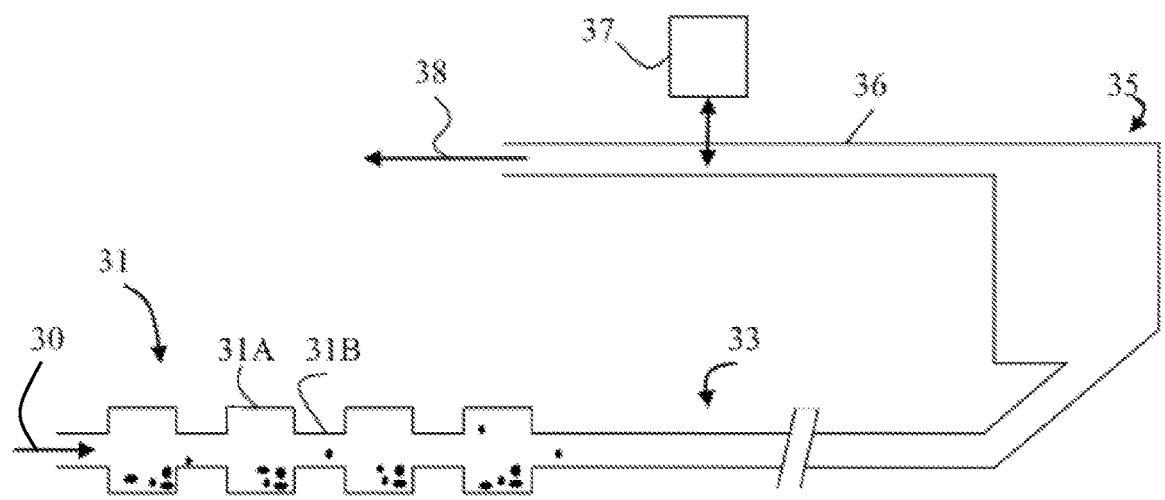
FIG. 5 illustrates an exemplary apparatus.

FIG. 5 illustrates an exemplary apparatus. In FIG. 5 there is shown in a illustrative schematic view of the fractionation and measurement system. Sample and water input stream is denoted with the numeral 30 and output stream with numeral 38. A first flow chamber 31 may be a disintegration channel 31 provided with expansions 31A and narrow parts 31B such that depressions are formed to the region of the expansion 31A. The disintegration channel 31 serves to gradually release particles according to their size and/or mass to a FFF channel 33 following the disintegration channel 31. The fractionation proceeds in the FFF channel 33. A homogenizer tube 35 which is an optional part, comprises a vessel with a larger cross-sectional area than the FFF channel 33 and homogenizes the particle populations exiting the FFF channel into one population. From the homogenizer tube 35, the fractionated sample is conducted via a conduit 36 to a measurement device 37 which is arranged to measure the desired physical and/or chemical property of the sample. The first flow chamber 31 may also be a fractionator of the type where particle separation into particle populations is based on particle settling, centrifugal separation or filtering according to the mass or size (or both) of the particles. Also, the sample may be fractionated as pretreated or untreated.

The fractionation of the sample may be carried out in the apparatus by means of one or more of filtration, centrifugation, sedimentation, column flow fractionator, tube fractionator, field flow fractionation (FFF), and disintegration channel assisted field flow fractionator. The term "field flow fractionation" (FFF) herein means a separation technique where a field is applied to a fluid suspension or solution pumped through a separation channel, perpendicular to the direction of flow, in order to cause separation of the particles present in the fluid, dependent on their differing mobilities under the force exerted by the field. Herein, the field is typically a gravitational field. Preferably, the fractionation is based on field flow fractionation (FFF). The fractionation of the sample may be carried out e.g. as described in WO 2013/175 077 or WO 2015/075 319.

Figure 1B:
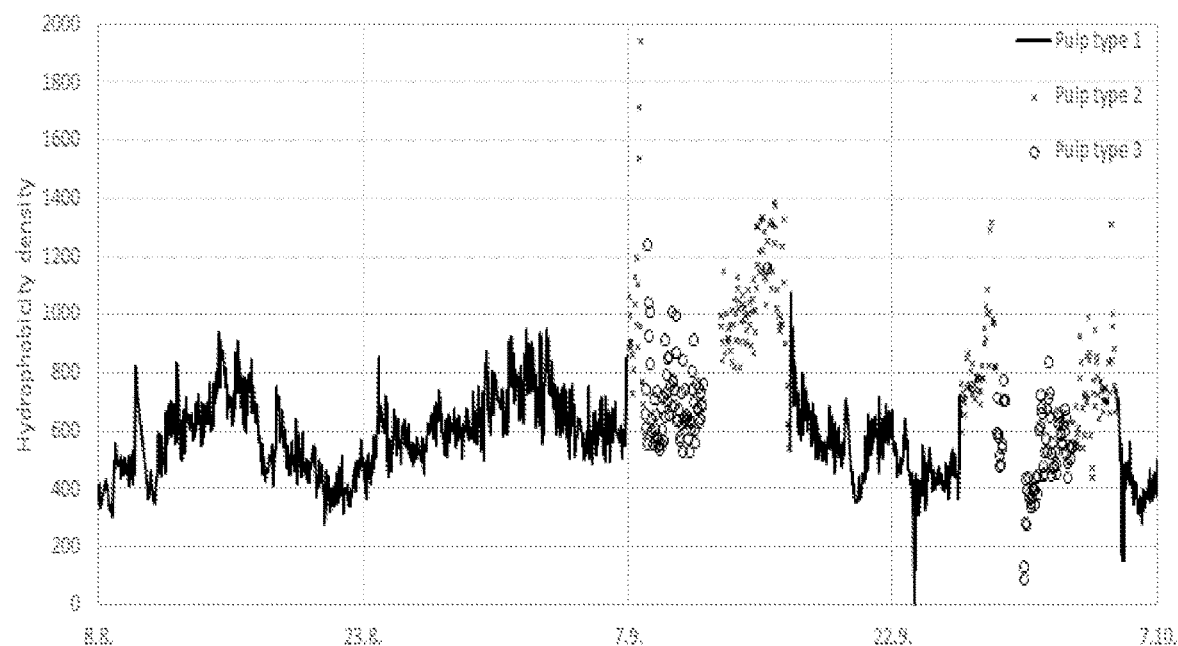

The output signals of the online sensors in the online system are fluorescence intensity signal and light scattering intensity signal. The ratio of the sum of fluorescence intensity signal to the sum of light scattering intensity signal is calculated, which ratio correlates directly with hydrophobicity index of the sample fractions when a hydrophobic dye such as Nile red is added to the sample. FIGS. 1A and 1B show an example of the hydrophobicity density for different pulp types. FIGS. 1A and 1B show that the pulp type (pulp type 2) having the highest hydrophobicity density, has the highest pitch concentration. FIGS. 1A and 1B also show that the pulp type (pulp type 1) having the lowest hydrophobicity density, has the lowest pitch concentration.

The system may comprise means of interpreting the results and to extract key variables for particle size and hydrophobicity index of a sample. The method may comprise pre-treatment and separation of samples in order to achieve the objectives is described.

The hydrophobicity index of individual fractions or the whole sample is used for monitoring the performance of chemicals by controlling the chemicals (e.g. controlling the dosage of chemical) and optimization of chemical dosing or chemical program (type of chemicals, chemical dosages, dosing points of chemicals in the process).

An on-line analysis method and system are disclosed, to monitor and control liquids such as aqueous suspensions or filtrates that contain solid matter in pulp industry.

The technology presented herein may be widely applied in the pulp industry, paper industry and/or any other bioindustry, for example, in wet end monitoring, broke treatment, stickies control of recycled pulp and chemical/mechanical pulp treatment including bleaching and dry section. It may be used for online monitoring of particle populations such as colloids, white pitch, wood pitch, stickies, fines, fillers, fibers, or agglomerates, and their hydrophobicity. The online system enables real-time problem solving and optimization of chemistry in a pulp or paper mill.

The method may be an on-line method. However, the sampling and measurement may also be performed manually by using a portable device. In the on-line method, the sampling, fractionation and measurements may be performed at a pre-set basis, intermittent basis, and/or continuous basis.

One or more chemicals may be used that modify the size and or surface characteristics of hydrophobic particles. The information obtained on the hydrophobicity density of the particles in the sample or fraction(s) may be utilized to form a control loop for the addition of one or more chemicals (dosage and/or type of the chemical), which may be used to control the amount/concentration of hydrophobic particles. The chemical(s) may include at least one of a fixative, a detackifier, dispersant, surfactant, and retention aid. The chemicals may be added to wet pulp. The chemicals may be added e.g. before the head box of the pulp process or in the wet end of the paper making process.

The method may include a correlating step where the hydrophobicity index obtained for the sample, is compared to a calibration curve predetermined for the analysis system, wherein the calibration curve indicates the correlation between the concentration of hydrophobic contaminants in the pulp stream (or diluted mass) and the hydrophobicity index of the sample.

Thus the pitch and/or other hydrophobic material in the pulp may be quantified. The amount of pitch in the pulp affects the pulp quality e.g. with regard to runnability on a paper machine. Pitch decreases the pulp quality e.g. by making it tackier.

The hydrophobicity density of the particles may be utilized to deduce the concentration of wood pitch in the aqueous stream on the basis of a predefined correlation between the concentration of the pitch particles and the hydrophobicity density. However, in an embodiment, it is not necessary to determine the correlation. Instead of the absolute pitch concentration, the method may comprise determining a hydrophobicity index level whereby the process (pulp drying machine or paper/board machine) works well, i.e. there are no problems caused by the wood pitch.

In an embodiment, the dosing of pulp washing water into the aqueous stream is controlled based on the calculated hydrophobicity density of the particles in the sample and/or based on the calculated hydrophobicity density of the particles in the fraction.

In an embodiment, the method comprises, based on the calculated hydrophobicity density, controlling the amount and/or type of chemical(s) added to the aqueous stream, to control the concentration of hydrophobic contaminants.

The method and system enable on-line monitoring the pitch concentration in cellulose pulp. The pulp process is monitored on-line by monitoring the concentration of pitch in pulp suspension or filtrates or dilutes of the pulp process. An on-line value for the concentration of pitch in the pulp process is obtained. The monitoring may also be performed batchwise and/or by means of a portable device.

The on-line analysis system may be used for monitoring hydrophobic particles in the pulp or paper making process. The system may be used to analyse the particle size and hydrophobicity distributions of the sample. The analysis system is able to identify e.g. the effect of one or more chemicals, e.g. a fixing agent, on the hydrophobic particle amount or distribution.

The method comprises measuring by optical measurement at least one of said particle populations to produce measurement signals representative of the amount and/or properties of the particles, processing said measurement signals to extract the fluorescence intensity values and the light scattering intensity values of each particle population or of the whole sample, wherein the processing of said measurement signals may include filtering, averaging and base-line correction of said signals.

Hydrophobicity as such refers to a tendency of nonpolar substances to aggregate in an aqueous solution and exclude water molecules. Hydrophobic material means "water-fearing" material, and hydrophobicity describes the segregation of water and nonpolar substances, which maximizes hydrogen bonding between molecules of water and minimizes the area of contact between water and nonpolar molecules. Hydrophobicity leads to separation of a mixture of e.g. oil and water into its two components.

The pulp stream or sample may include particles such as colloidal particles, fine particles, agglomerates, and/or fibers.

Colloidal particles are small particles, typically within the size range of 0.1 μm-5 μm.

Fine particles (fines) are typically within the size range of 5-100 μm.

Agglomerates are typically within the size range of more than 10 μm.

Fibers are typically within the size range of 0.7-2.9 mm (length) and 16-35 mm (diameter). The fiber length/size may vary depending on the tree species from which the pulp originates and on whether it is from springwood or summerwood, as follows. Eucalyptus: fiber length 1 mm, fiber diameter 16 μm; birch: fiber length 1.1 mm, fiber diameter 22 μm; aspen: fiber length 0.8 mm, fiber diameter 18 μm; acacia: fiber length 0.7 mm, fiber diameter 20 μm; pine: fiber length 2.9 mm, fiber diameter from 20 mm (summerwood) to 35 mm (springwood); spruce: fiber length 2.9 mm, fiber diameter from 19 mm (summerwood) to 33 mm (springwood).

In an embodiment, techniques for fractionating and/or analysing pulp samples and/or for controlling pulp process discussed in WO 2013/175 077 and/or WO 2015/075 319 A1 may be utilized.

EXAMPLE 1

A pulp machine may use different types of pulps. The hydrophobicity density of particles for three different pulp streams (white water streams) were measured over a time period (from 22$^{nd}$ June to 6$^{th}$ August, see FIG. 1A; and from 8$^{th}$ August to 7$^{th}$ October, see FIG. 1B). In FIGS. 1A and 1B, pulp type 2 originates from tree species that have high wood pitch content. Pulp type 3 originates from tree species with a lower amount of wood pitch. This may be clearly seen from the measured hydrophobicity density in FIGS. 1A and 1B. The hydrophobicity density is the highest for pulp type 2. Pulp type 1 has the lowest wood pitch content.

EXAMPLE 2

Figure 2:
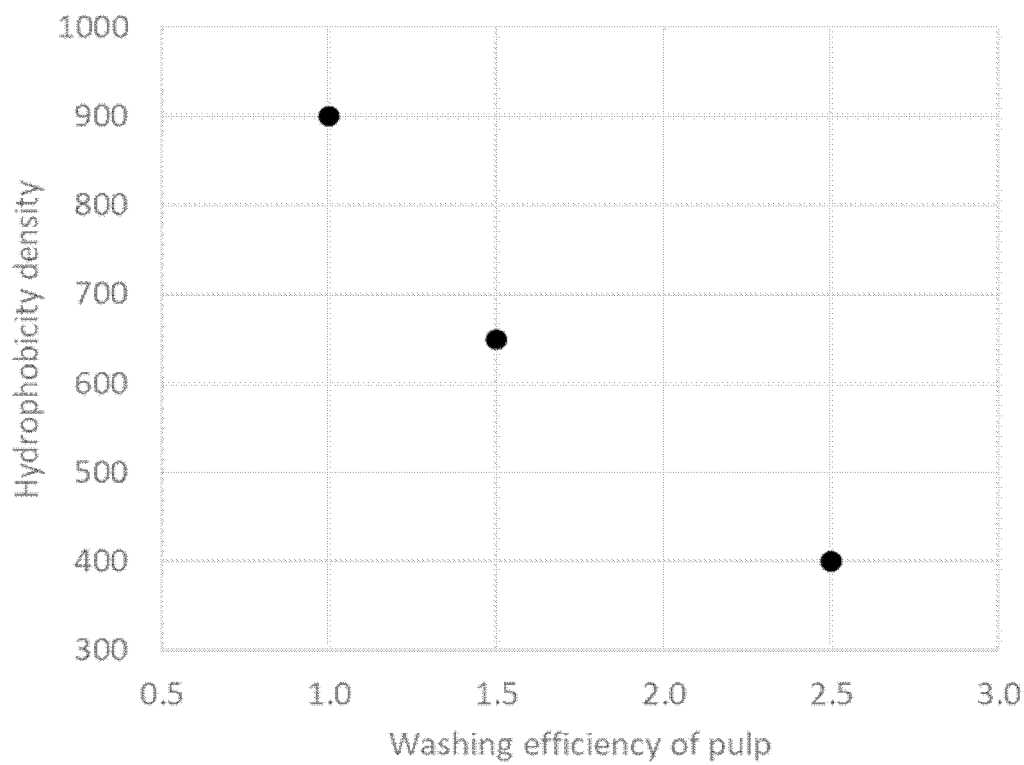
FIG. 2 shows the effect of pulp washing on the hydrophobicity density.

The effect of washing on the hydrophobicity index was tested. FIG. 2 shows how the changes in pulp washing efficiency affected the hydrophobicity density. When the washing efficiency was increased by 1.5 and 2.5 times, the hydrophobicity index clearly decreased.

EXAMPLE 3

Figure 3:
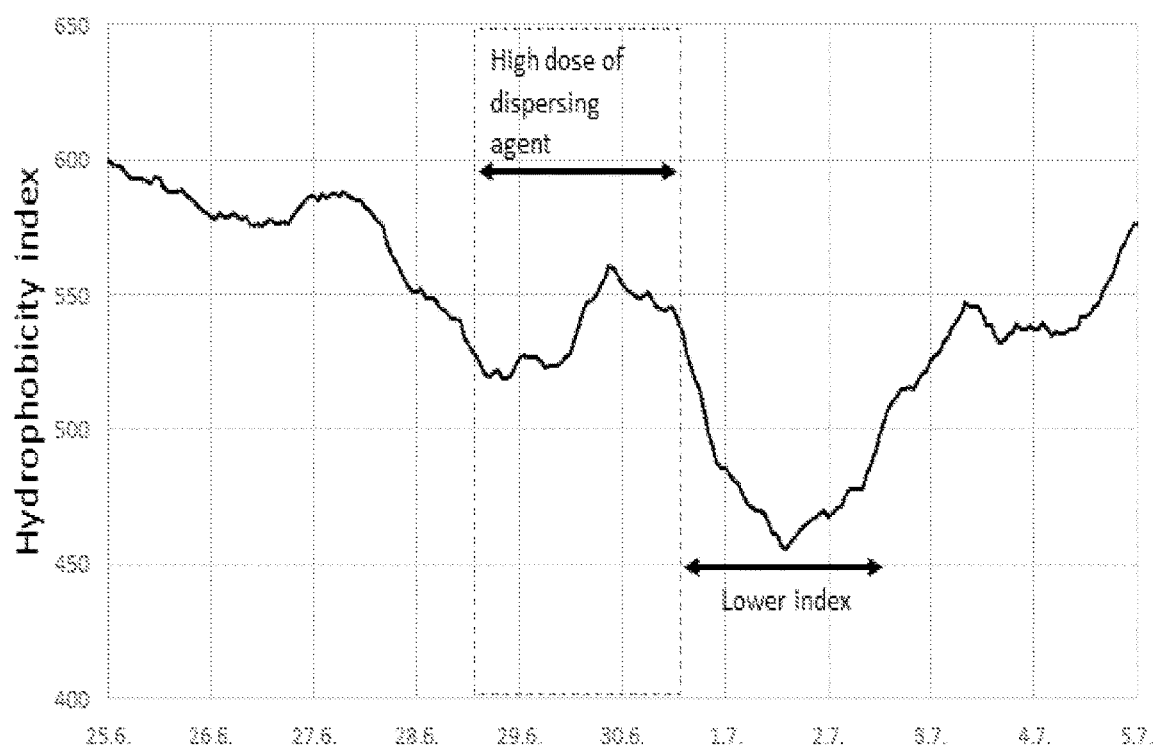
FIG. 3 shows the effect of chemical dosing on the hydrophobicity index of the pulp stream.

The effect of the changes in the dispersing agent dosing on the hydrophobicity index was tested. The results are shown in FIG. 3. With a higher chemical dosage, the hydrophobicity density decreased from 600 to about 450. A time delay between the dosing point and the measuring point was 1.5 days. An increase in the hydrophobicity index was clearly detected after the chemical dosage was returned back to basic dosage level.

Figure 6:
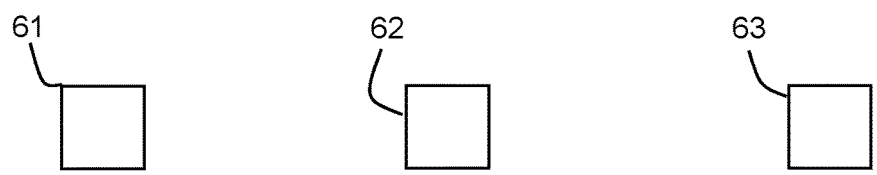
FIG. 6 illustrates the dyeing means, computing means and control means.

FIG. 6 illustrates labeled representations of a dyer 61, computer 62 and controller 63. The labeled representations do not provide any indication of size or relative position of the illustrated components.

The above components prove the technical performance of the exemplary method. The hydrophobicity density describes well the content of hydrophobic components in the pulp stream.

It will be obvious to a person skilled in the art that, as the technology advances, the inventive concept can be implemented in various ways. The invention and its embodiments are not limited to the examples described above but may vary within the scope of the claims.

The invention claimed is:

1. A method for monitoring and controlling hydrophobic contaminants in an aqueous stream of a pulp or papermaking process, the method comprising:
    conducting a sample of the aqueous stream to an optical measurement device, the sample containing solid particles;
    adding hydrophobic dye to the sample;
    fractionating the sample into two or more fractions according to particle size and/or particle mass; and
    measuring fluorescence intensity values and light scattering intensity values for each of the two or more fractions; the method further comprising:
    adding together the fluorescence intensity values of the fractions thus obtaining a sum of the fluorescence intensity values;
    adding together the light scattering intensity values of the fractions thus obtaining a sum of the light scattering intensity values;
    calculating a hydrophobicity density of the particles in the sample by dividing the sum of the fluorescence intensity values with the sum of the light scattering intensity values, and
    monitoring and controlling a concentration of hydrophobic contaminants in the aqueous stream based on the calculated hydrophobicity density of the particles in the sample,
or
    adding together the fluorescence intensity values of a fraction thus obtaining a sum of the fluorescence intensity values in the fraction,
    adding together the light scattering intensity values of the fraction thus obtaining a sum of the light scattering intensity values in the fraction,
    calculating a hydrophobicity density of the particles in the fraction by dividing the sum of fluorescence intensity values of the fractions with the sum of light scattering intensity values of the fraction; and
    monitoring and controlling the concentration of hydrophobic contaminants in the aqueous stream based on the calculated hydrophobicity density of the particles in the fraction.

2. A method as claimed in claim 1, wherein the method further comprises:
    controlling the concentration of hydrophobic contaminants in the aqueous stream by
    manually and/or automatically adjusting a dosing of at least one chemical into the aqueous stream; and/or
    manually and/or automatically adjusting a dosing of pulp washing water into the aqueous stream.

3. A method as claimed in claim 2, further comprising:
    controlling the dosing of pulp washing water into the aqueous stream based on the calculated hydrophobicity density of the particles in the sample and/or based on the calculated hydrophobicity density of the particles in the fractions.

4. A method as claimed in claim 1, the method further comprising:
utilizing the calculated hydrophobicity density of the particles to deduce a concentration of wood pitch in the aqueous stream based on a predefined correlation between the concentration of the pitch particles and the hydrophobicity density.

5. A method as claimed in claim 1, comprising, performing continuously as a function of time:
conducting the sample of the aqueous stream to the optical measurement device, the sample containing solid particles;
adding hydrophobic dye to the sample;
fractionating the sample into the two or more fractions according to particle size and/or particle mass;
measuring the fluorescence intensity values and the light scattering intensity values for each of the two or more fractions;
adding together the fluorescence intensity values measured continuously as a function of time, thus obtaining the cumulative sum of the fluorescence intensity values;
adding together the light scattering intensity values measured continuously as a function of time, thus obtaining the cumulative sum of the light scattering intensity value;
calculating the hydrophobicity density of the particles in the sample by dividing the cumulative sum of the fluorescence intensity values with the cumulative sum of the light scattering intensity values; and/or
calculating the hydrophobicity density of the particles in the fraction by dividing the fluorescence intensity values with the light scattering intensity values.

6. A method as claimed in claim 1, wherein the fractionating comprises:
fractionating the sample into one or more of a colloid fraction, fines fraction, agglomerates fraction, and fiber fraction.

7. A method as claimed in claim 1, wherein the hydrophobic contaminants are:
microstickies in a form of colloidal particles and/or particles adsorbed onto fine particles; and/or macrostickies.

8. A method as claimed in claim 1, wherein the hydrophobic contaminants are pitch particles in a form of: colloidal particles, agglomerates and/or particles adsorbed onto fibers.

9. A method as claimed in claim 1, comprising:
based on the calculated hydrophobicity density, controlling an amount and/or type of at least one chemical added to the aqueous stream, to control the concentration of hydrophobic contaminants.

10. A method as claimed in claim 1, comprising:
based on the calculated hydrophobicity density, controlling a dosing into the aqueous stream of one or more of a dispersant, fixative, detackifier, retention aid, and surfactant.

11. A method as claimed in claim 1, comprising:
taking the sample of the aqueous stream from filtrate water, dilute mass, or wire water.

12. A method as claimed in claim 1, comprising:
adding chemicals and/or pulp washing water to the aqueous stream at a position that is located at a sample taking position, upstream of the sample taking position and/or downstream of the sample taking position.

13. An apparatus for monitoring and controlling hydrophobic contaminants in an aqueous stream of a pulp or papermaking process, the apparatus comprising:
a sampler configured to conduct a sample of the aqueous stream, the sample containing solid particles;
a dyer configured to add hydrophobic dye to the sample;
a fractionator configured to fractionate the sample into two or more fractions according to particle size and/or particle mass;
an optical measurement device configured to measure fluorescence intensity values and light scattering intensity values for each of the two or more fractions; and
a computer configured to:
add together the fluorescence intensity values of the fractions thus obtaining a sum of the fluorescence intensity values, and to add together the light scattering intensity values of the fractions thus obtaining a sum of the light scattering intensity values; and
calculate a hydrophobicity density of the particles in the sample by dividing the sum of the fluorescence intensity values with the sum of the light scattering intensity values;
or
add together the fluorescence intensity values of a fraction thus obtaining a sum of the fluorescence intensity values in the fraction, and to add together the light scattering intensity values of the fraction thus obtaining a sum of the light scattering intensity values in the fraction, and
calculate a hydrophobicity density of the particles in the fraction by dividing the sum of the fluorescence intensity values of the fraction with the sum of the light scattering intensity values of the fraction,
the apparatus including a controller configured to monitor and control a concentration of hydrophobic contaminants in the aqueous stream based on either:
the calculated hydrophobicity density of the particles fraction, or
the calculated hydrophobicity density of the particles in the sample.

14. An apparatus as claimed in claim 13, wherein the controller is configured to:
control the concentration of hydrophobic contaminants in the aqueous stream by:
automatically adjusting the dosing of at least one chemical into the aqueous stream; and/or
automatically adjusting a dosing of pulp washing water into the aqueous stream.

15. An apparatus as claimed in claim 13, wherein the computer is configured to:
utilize the hydrophobicity density of the particles to deduce a concentration of pitch in the aqueous stream based on one of a predefined correlation between the concentration of the pitch particles and the hydrophobic density.

16. An apparatus as claimed in claim 13,
wherein the apparatus is configured to in operation, continuously as a function of time;
conduct the sample of the aqueous stream to the optical measurement device, the sample containing solid particles;
add hydrophobic dye to the sample;
fractionate the sample into two or more fractions according to particle size and/or particle mass;

measure fluorescence intensity values and light scattering intensity values for each of the two or more fractions;

add together the fluorescence intensity values measured continuously as a function of time, thus obtaining a cumulative sum of the fluorescence intensity values;

add together the light scattering intensity values measured continuously as a function of time, thus obtaining a cumulative sum of the light scattering intensity values;

calculate the hydrophobicity density of the particles in the sample by dividing the cumulative sum of the fluorescence intensity values with the cumulative sum of the light scattering intensity values; and/or calculate the hydrophobicity density of the particles in the, fractions by dividing the fluorescence intensity values with the light scattering intensity values.

17. An apparatus as claimed in claim 13, wherein the fractionator is configured to:
fractionate the sample into one or more of a colloid fraction, fines fraction, agglomerates fraction, and fiber fraction.

18. An apparatus as claimed in claim 13, wherein the controller is configured to, based on the calculated hydrophobicity density, control a dosing into the aqueous stream of one or more of a dispersant, fixative, detackifier, retention aid, and surfactant.

19. An apparatus as claimed in claim 13, wherein the controller is configured to send signals to cause adding chemicals and/or pulp washing water to an aqueous stream at a position that is located at a sample taking position, upstream of the sample taking position and/or downstream of the sample taking position.

* * * * *